(12) United States Patent
Kohlbrenner et al.

(10) Patent No.: US 10,026,215 B2
(45) Date of Patent: Jul. 17, 2018

(54) METHOD AND APPARATUS FOR DIGITIZING THE APPEARANCE OF A REAL MATERIAL

(71) Applicant: X-Rite Switzerland GmbH, Regensdorf (CH)

(72) Inventors: Adrian Kohlbrenner, Thalwil (CH); Martin Rump, Winterscheid (DE); Beat Frick, Buchs (CH); Christopher Schwartz, Bonn (DE)

(73) Assignee: X-Rite Switzerland GMBH, Regensdorf (CH)

( * ) Notice: Subject to any disclaimer, the term of this patent is extended or adjusted under 35 U.S.C. 154(b) by 452 days.

(21) Appl. No.: 14/673,312

(22) Filed: Mar. 30, 2015

(65) Prior Publication Data

US 2016/0171748 A1 Jun. 16, 2016

(30) Foreign Application Priority Data

Dec. 11, 2014 (EP) ..................................... 14197409

(51) Int. Cl.
*H04N 5/225* (2006.01)
*G06T 15/10* (2011.01)
*G01N 21/57* (2006.01)

(52) U.S. Cl.
CPC ............. *G06T 15/10* (2013.01); *G01N 21/57* (2013.01); *H04N 5/2256* (2013.01); *G06T 2200/04* (2013.01)

(58) Field of Classification Search
CPC combination set(s) only.
See application file for complete search history.

(56) References Cited

U.S. PATENT DOCUMENTS 2,353,512 A * 7/1944 Simmon .............. G03B 27/545
355/67
6,084,663 A 7/2000 Seng
(Continued)

FOREIGN PATENT DOCUMENTS

| EP | 0452905 | 10/1991 |
| EP | 1054376 A2 * | 11/2000 |
| WO | WO 2014091214 | 6/2014 |

OTHER PUBLICATIONS

European Search Report dated May 29, 2015 for European Patent Application No. 14197409.7.
(Continued)

*Primary Examiner* — Janese Duley
(74) *Attorney, Agent, or Firm* — Hahn Loeser & Parks, LLP

(57) ABSTRACT

A system and method of determining data representing a mapping of optical signals described by image data of a reflecting surface of a structure to a three-dimensional surface geometry of the reflecting surface is provided. At least first, second and third light sources are provided, comprising a broadband point light source, a spectrally variable point light source and a movable linear broadband light source, respectively. First, second and third images are acquired, corresponding to each light source. Surface geometry data describing a three-dimensional surface geometry of the reflecting surface is acquired. Based on the image data and the surface geometry data, reflecting surface mapping data describing a mapping between the reflections described by the first image data, second image data and third image data, and the three-dimensional surface geometry of the reflecting surface is determined.

16 Claims, 7 Drawing Sheets

(56) References Cited

U.S. PATENT DOCUMENTS

| | | | |
|---|---|---|---|
| 8,872,811 B1 | 10/2014 | Rump et al. | |
| 2003/0001859 A1* | 1/2003 | Sloan | G06T 15/60 345/584 |
| 2003/0231174 A1* | 12/2003 | Matusik | G06T 9/001 345/419 |
| 2004/0263510 A1* | 12/2004 | Marschner | G06T 13/40 345/419 |
| 2008/0232679 A1* | 9/2008 | Hahn | G06K 9/2036 382/154 |
| 2010/0246174 A1 | 9/2010 | Ido et al. | |
| 2014/0268160 A1 | 9/2014 | Debevec | |

OTHER PUBLICATIONS

Woodham, R. J., Photometric Stereo: A Reflectance Map Technique for Determining Surface Orientation From Image Intensity, $22^{nd}$ Proc. SPIE 0155, Image Understanding Systems and Industrial Applications I, 136 (Jan. 9, 1979), pp. 136-143.

Kajiya, J. T., The Rendering Equation, ACM SIGGRAPH Computer Graphics, vol. 20, No. 4, ACM, pp. 143-150, 1986.

Malzbender, T. et al., Polynomial Texture Maps, Proceedings of the 28thannual conference on Computer Graphics and Interactive Techniques, pp. 519-528, ACM, 2001.

Sloan, P.-P. et al., Precomputed Radiance Transfer for Real-Time Rendering In Dynamic, Low-Frequency Lighting Environments, ACM Transactions on Graphics (TOG), vol. 21, No. 3, pp. 527-536, ACM, 2002.

Salvi, J. et al., A State of the Art in Structured Light Patterns for Surface Profilometry, Pattern Recognition 43, No. 8 (2010): pp. 2666-2680.

Schwartz, C. et al., Dome II: A Parallelized BTF Acquisition System, in Proceedings of Eurographics Workshop on Material Appearance Modeling: Issues and Acquisition, Zaragoza, Spain, pp. 25-31, Eurographics Association, Jun. 2013.

* cited by examiner

METHOD AND APPARATUS FOR DIGITIZING THE APPEARANCE OF A REAL MATERIAL

RELATED APPLICATIONS

This Application claims the benefit of and priority to European Patent Application No. 14147409.7, filed Dec. 11, 2014.

TECHNICAL FIELD

The present invention is directed to a method of determining data representing a mapping of optical signals described by image data of a reflecting surface of a structure to a three-dimensional surface geometry of the reflecting surface, and an apparatus for obtaining data representing optical signals received from a reflecting surface of a structure which comprises a computer configured to execute a program for performing the aforementioned method.

TECHNICAL BACKGROUND

When measuring optical properties of reflective surfaces and determining the resulting spatially varying bidirectional reflectance function, one issue is to have improved measurement of gloss characteristics. Using only point light sources having fixed positions in an apparatus for irradiating a sample to determine the reflective properties of the sample may lead to a loss of spatial information for example in cases of anisotropic reflectance of the sample. Such a prior art approach is disclosed for example in Schwartz, C. et al., DOME II: A Parallelized BTF Acquisition System, in Proceedings of Eurographics Workshop on Material Appearance Modeling: Issues and Acquisition, Zaragoza, Spain, pages 25-31, Eurographics Association, June 2013. Another prior art approach is disclosed in U.S. Pat. No. 8,872,811 B1 which teaches to interpolate the positions of sensors of a measurement apparatus to make up for possible undersampling. This however involves some uncertainty in the correctness of the measurement data thus obtained and may lead to increased computational effort due to generation of additional data.

The invention therefore has the object of providing a method and apparatus capable of providing improved gloss measurement when determining a spatially varying bidirectional reflectance function for a specific structure while keeping the amount of data generated at a bearable level.

This object is reached by the subject-matter of any appended independent claim. Further features and aspects of the present invention are disclosed in the following and contained in the subject-matter of the dependent claims. Different features can be combined in accordance with the invention as long as technically sensible and feasible. For example, a feature of one embodiment which has the same or similar function of another feature of another embodiment can be exchanged. For example, a feature of one embodiment which supplements a further function to another embodiment can be added to the other embodiment.

SUMMARY

In order to reach the aforementioned object, the present invention provides, in a first aspect, a digital data processing method of determining data representing a mapping of optical signals described by image data of a reflecting surface of a structure to a three-dimensional surface geometry of the reflecting surface. The structure can be any kind of (three-dimensional) structure, for example a corporeal (specifically, tangible) structure. For example, the structure is at least one of a textile structure and/or a plastic structure and/or a leather structure and/or a metal structure and/or a painted structure. The reflecting surface is an exterior surface (for example, a textured surface) of the structure onto which measurement light is emitted and from which it is reflected. The method comprises the following features (the following steps) which are constituted to be executed by for example a computer.

In a (for example first) exemplary step, the method acquires first image data describing (for example defining) an image (a first image) of a reflection of light of a first type from a reflecting surface of the structure. As an example, the first type of light is broadband point light which is emitted for example from a white light-emitting diode (LED) or an equivalent light source.

In a (for example second) exemplary step, the method acquires second image data describing (for example defining) an image (a second image) of a reflection of light of a second type from the reflecting surface of the structure. As an example, the second type of light is spectral (non-white) point light which is emitted for example from a coloured (non-white) LED or a white LED which is fitted with a colour filter or an equivalent light source.

In a (for example third) exemplary step, the method acquires third image data describing (for example defining) an image (a third image) of a reflection of light of a third type from the reflecting surface of the structure. As an example, the third type of light is broadband linear light which is emitted from a linear light source, for example a fluorescent tube or a linear array of LEDs. The linear light source is for example elongated in one dimension and of finite (smaller) thickness in the other dimensions. For example, the linear light source comprises only one fluorescent tube or a linear array of LEDs comprising only one line of LEDs. Alternatively, the linear light source may be embodied by a monitor (such as a flat screen monitor, for example a liquid crystal display monitor), which is programmed to display a linear graphical feature of predetermined geometry (for example, in the shape of a relatively thin line made up by a predetermined number of pixels in the line direction and/or the column direction of the display reference system), specifically at a predetermined brightness. Using a monitor in that way as the linear light source provides the advantage of being able to adapting the geometry of the linear light source as required by appropriately controlling the monitor to display the linear light. Furthermore, a monitor provides the advantage of being able to produce not only white but—if desired—also spectral (coloured, i.e. non-white) light if it is appropriately controlled. In one example, the linear light source is disposed below a support part on which the structure is supported which allows for transmission measurement of the structure with the light of the third type if the detection system is at least partly disposed on the other side of the structure when viewed from the position of the linear light source.

From the above, it is clear that the first type of light, second type of light and third type of light constitute three different types of light. Specifically, the three types of light constitute each a different type of light. The disclosed method therefore uses at least three different types of light for illuminating the reflecting surface. It is also within the framework of the disclosed method to use more than three different types of light such as four or five different types of light. Combining the three types of light including the linear light to derive reflectance signals provides the advantage of improved gloss measurement which is highly sensitive to spatial undersampling of reflection signals generated by point light sources (such as the above-described broadband and spectral LEDs). Such undersampling generally occurs due to a defined and generally fixed position of the point light source with respect to the structure and to the detector. The inventors unexpectedly found out that gloss measurement using only point light sources can be drastically improved by combining it with reflection signals received from an extended light source such as a linear light source, thereby avoiding the effects of undersampling while maintaining the amount of data to be processed at an acceptable level in view of processing time and computational resources including electronic data storage space.

In a (for example fourth) exemplary step, the method acquires surface geometry data describing (for example defining) a surface geometry of the reflecting surface. The surface geometry is in one embodiment defined by the (relative) elevation (height spacing and/or vertical spacing) between individual elements of the reflecting surface. In another embodiment, the surface geometry is defined not by height information for each such element but by information defining the orientation of the surface element. That orientation may be defined in a global coordinate system or relative between the elements of the reflecting surface. In another embodiment the surface geometry is given as a huge set of points in 3D space. In another embodiment the surface geometry is given as a triangle or quad mesh consisting of vertices and flat triangles or quads spanned between the vertices. In another embodiment, the surface geometry is given as a combination of either the height field, point cloud or mesh together with the orientation stored at a different (for example higher) resolution.

In a (for example fifth) exemplary step the structured light patterns of the fourth kind of light source can be used to determine parameters of the sub-surface scattering of light under the surface of the structure (this effect is also called translucence). The sub-surface scattering in principle is a reflexion phenomenon which occurs in the interior of the structure. Hence, any terminology in this disclosure referring to the optical phenomenon of reflection also encompasses the phenomenon of translucence. However, in the present disclosure, any terminology referring to the optical phenomenon of reflection may alternatively be understood to denote exclusively reflections which occur on the exterior surface of the structure. In one example, a pattern consisting of single points with a certain distance to each other can be projected to the structure's surface. In a respective image of the reflecting surface illuminated by this distant spots, a measure of the light scattered under the surface can be extracted from the non-illuminated parts of the surface and a model can be fitted to the extracted measurement values.

According to a first embodiment of the method, the surface geometry data describes (for example defines) a height field of the reflecting surface. The surface geometry data is for example acquired based on (specifically, from) fourth image data describing an image (a fourth image) of a reflection of light of a fourth type from the reflecting surface of the structure. The fourth type of light is a type of light different from the first type, second type and third type of light. In one example, the fourth type of light is structured light, for example light emitted from source of structured light such as a projector (light projector). Structured light is light which exhibits for example a certain pattern (for example visual pattern), i.e. light which is emitted in a certain (specifically, two-dimensional) pattern. The image described by the fourth image data is therefore also called a structured light image. This image describes a topography, for example a relief, of the reflecting surface. The height field describes the elevation (for example, the relative elevation) of elements of the reflecting surface. For example, the height field describes the elevation (i.e. the spacing/distance/coordinate difference in a third dimension, for example the vertical direction) of at least one of those elements relative to at least one other one of those elements. This height field can be reconstructed from the structured light image by generating a point cloud according to a method from the prior art, an overview being given by Salvi, J. et al., A state of the art in structured light patterns for surface profilometry, Pattern Recognition 43, no. 8 (2010): pp. 2666-2680, and in consideration of the geometric calibration of a detection system used for detecting the reflections of the structured light. The resolution of the height field depends on the spatial sampling used for detection of the reflection signals of the fourth type of light. The height field allows for determination of the orientation of the elements of the reflecting surface by basic geometric calculations.

According to a second embodiment of the method in accordance with the first aspect, the surface geometry data describes (for example defines) a normal field of the reflecting surface. In that case, the surface geometry data is acquired for example based on at least one of the first image data, second image data and third image data. The normal field describes the orientations of elements of the reflecting surface. For example, the orientation of each element is defined by the direction of its surface normal. The normal field is a data set comprising information about the desired surface normal. The normal field can be obtained based on (for example from) the first image, second image and third image under the assumption of the reflecting surface being a diffusely reflecting surface and determining the orientation of each surface element from the brightness determined for each surface element. The normal field can also be refined for non-diffuse surfaces by incorporating the gloss information also derived from the first, second and third image data. This is done using a non-linear optimization method.

In summary, the surface geometry data describes (for example defines) at least one of the aforementioned height field and the aforementioned normal field.

In a (for example sixth) exemplary step, the method determines, based on the first image data and the second image and the third image data and the surface geometry data, reflecting surface mapping data describing (for example defining) a mapping between the reflections described by the first image data, second image data and third image data, and the three-dimensional surface geometry of the reflecting surface. For example, the optical signals (specifically, reflection signals) are mapped onto the three-dimensional surface geometry. The mapping is established for example by projecting the images described by the first image data, second image data and third image onto the surface geometry described by the surface geometry data. The three-dimensional geometry is for example described (for example defined) by information contained in the surface geometry data allowing determination of the orientation of the surface elements such as at least one of the height field and the normal field of the reflecting surface.

The images described by the first image data, second image data, third image data and—if applicable—fourth image data are for example digital images generated by a detection system comprising at least one detection unit such at least one digital camera (in other examples, a plurality of digital cameras, for example exactly three digital cameras)

which detects the reflection signals of the light of the first type, second type and third type and—if applicable—also the fourth type. The detection system therefore is sensitive specifically in the spectral ranges of the light of the first type, the second type the third type and—if applicable—the fourth type.

In a second aspect, the invention is directed to a method of determining data describing (for example defining or representing) a spatially varying bidirectional reflectance distribution of the reflecting surface of the structure, the method comprising the following steps which are constituted to be executed by a computer:

1. The above-described digital data processing method of determining data representing a mapping (according to the first aspect) is performed.
2. Reflectance function data describing a bidirectional reflectance distribution function (BRDF) model is acquired. The reflectance function data comprises for example code representing a mathematical expression of a BRDF model.
3. Based on the reflecting surface mapping data and the reflectance function data, reflectance distribution data describing the spatially varying bidirectional reflectance distribution of the reflecting surface is determined. This is for example done by fitting the BRDF model to the reflectance information contained in the first image data, second image data and third image data in consideration of the surface geometry data, for example per surface position. For the fitting process, a non-linear optimisation algorithm is used. The resulting SVBRDF (spatially varying bidirectional reflectance distribution function) parameters defining the spatially varying bidirectional reflectance distribution of the reflecting surface are stored in a digital file comprising the reflectance distribution data on a non-volatile electronic memory device.

In a third aspect, the invention is directed to a method of offline rendering of a digital image representation (displaying of a pre-rendered digital image representation which specifically is visually recognizable and therefore human-readable) of a reflecting surface of a structure, the method comprising the following steps which are constituted to be executed by a computer:

1. The above-described method of determining data describing a spatially varying bidirectional reflectance distribution for the reflecting surface of the structure (according to the second aspect) is performed.
2. Based on the reflectance distribution data, surface representation data is determined (for example, synthesized) which describes (for example defines) an image (a digital image) of the reflecting surface. The surface representation data is determined for example for a specific observation angle (elevation angle and azimuth at which the surface is virtually observed).
3. For example, the method in accordance with the third aspect comprises offline rendering (for example displaying) the information content of the surface representation data (i.e. the digital image representing the reflecting surface), for example on a display device such as a standard monitor or via a projector and a screen (projector screen, for example canvas screen). In a fourth aspect, the invention is directed to a method of determining data (for example, a model and parameters) describing (for example defining or representing) a shadow appearance (specifically, data describing a model and parameters defining a shadow appearance) of a reflecting surface of a structure, the method comprising the following steps which are constituted to be executed by a computer:

1. The above-described method of determining a reflectance distribution of the reflecting surface of the structure (according to the second aspect) is performed.
2. Based on the reflecting surface mapping data and at least one of the first image data, second image data and third image data, shadow appearance data is determined which describes (for example defines) an appearance of shadow for the reflecting surface. The shadow appearance parameters contained in the shadow appearance data which characterise the shadow appearance, can be stored in a digital file for later use. Specifically, the shadow appearance parameters can be stored in a single file together with the spatially varying bidirectional reflectance distribution parameters.

In a fifth aspect, the invention is directed to a method of real-time rendering of a digital image representation (i.e. displaying of digital image representation which is generated online and specifically is visually recognizable and therefore human-readable) of a reflecting surface of a structure, the method comprising the following steps which are constituted to be executed by a computer:

1. The above-described method of determining a reflectance distribution of the reflecting surface of the structure (according to the second aspect) is performed.
2. Based on the reflectance distribution data and optionally the shadow appearance data, surface representation data is determined which describes (for example defines) an image of the reflecting surface.
3. For example, the method in accordance with the fifth aspect comprises online (i.e. real-time) rendering (for example displaying) of the information content of the surface representation data (i.e. the digital image representing the reflecting surface), for example on a display device such as a standard monitor or via a projector and a screen (projector screen, for example canvas screen).

In a sixth aspect, the invention is directed to using the output of the method according to the second aspect as an input for further electronic data processing, for example in the framework of a method of determining a surface property (for example, at least one of gloss, haze, distinctness-of-image and brilliance described (for example defined) by a reflectance of a reflecting surface of a sample structure. Such a method would use the output of the method according to the second aspect, for example for comparison with a measurement taken for the sample such as it would be done on the framework of quality control for the respective surface property of the sample. That method is constituted to be executed by for example a computer.

In a seventh aspect, the invention is directed to a computer program which, when running on a computer or when loaded onto a computer, causes the computer to perform the method according to any one of the above-described aspects.

In an eight aspect, the invention is directed to a non-transitory computer-readable storage medium on which the aforementioned program is stored.

In the following, a ninth aspect of the invention will be described which is directed to an apparatus which is usable to conduct the method in accordance with the first to sixth aspects.

The description of the method features is also applicable to the analogous features of that apparatus.

In a first embodiment of the ninth aspect, the invention is directed to an apparatus for obtaining data representing optical signals received from a reflecting surface of a structure, the apparatus comprising:

a) at least one first light source configured to emit the light of the first type onto the reflecting surface;

b) at least one second light source configured to emit the light of the second type onto the reflecting surface;

c) at least one third light source configured to emit the light of the third type onto the reflecting surface; alternatively or additionally, the structure is transmissive for the light of the third type and the third light source is configured to emit the light of the fourth type through the structure (such that it is transmitted through the reflecting surface, for example transmitted through the reflecting surface to the detection system);

d) as explained above with regard to the method according to the first aspect, the first, second and third types of light constitute three different types of light;

e) a support part for supporting the structure (for example, a turntable onto which the structure may be placed for irradiation with the light according to the first type, second type, third type and—if applicable—fourth type);

f) a detection system configured to detect a first reflection signal of the light of the first type from the reflecting surface and to convert the first reflection signal into first image data describing an image of the reflecting surface of the structure;

detect a second reflection signal of the light of the second type from the reflecting surface and to convert the second reflection signal into second image data describing an image of the reflecting surface of the structure; and detect a third reflection signal or a transmission signal of the light of the third type from the reflecting surface and to convert the third reflection signal into third image data describing an image of the reflecting surface of the structure or to convert the transmission signal into third image data describing an image of the structure;

g) a computer which is operatively coupled to the detection system and configured to execute the computer program according to the seventh aspect and/or comprising the storage medium according to the eighth aspect.

The disclosed apparatus therefore uses at least three different types of light sources for illuminating the reflecting surface. It is also possible that the disclosed apparatus comprises more than three different types of light sources such as four or five different types of light sources configured to emit the corresponding number of different types of light.

In one example, the detection system is the detection system described in the context of the method in accordance with the first aspect.

In a second embodiment of the ninth aspect, the apparatus comprises at least one fourth light source configured to emit the light of the fourth type onto the reflecting surface;

wherein the detection system is configured to detect a fourth reflection signal or a transmission signal of the light of the fourth type from the structure and to convert the fourth reflection signal or the transmission signal into surface geometry data describing a height field of the reflecting surface of the structure;

wherein the at least one first light source is a broadband point light source, the at least one second light source is a spectral point light source, the third light source is a broadband linear light source, and the fourth light source is a source of structured light. The source of structured light is for example the one described in the context of the method according to the first aspect.

In a third embodiment of the ninth aspect, the detection system and the first light source, the second light source, the third light source and—as far as the device includes the further features of the second embodiment of the ninth aspect—the fourth light source are disposed in the hemisphere above the support part and at least one further light source configured to emit light of at least one of the first type, second type, third type and—as far as the device includes the further features of the preceding claim—fourth type is disposed in the hemisphere below the support part. For example, the first light source, the second light source, the third light source and—as far as the device includes the further features of the second embodiment of the ninth aspect—the fourth light source as well as the detection system are fastened to a holding part, for example to an at least partly spherical (for example, dome-shaped) structure, which is disposed above the support part and therefore in the hemisphere above the support part. Additionally, such a structure may be disposed below the support part so that the aforementioned types of light sources can also irradiate the structure from below, i.e. from the hemisphere below the support part so as to allow for measurement of transmissivity (for example transparency) or translucence of the structure.

Definitions

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital electronic processor (central processing unit or CPU) which executes the computer program elements and optionally a volatile memory (for example, a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is for example a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element).

The method in accordance with the invention is for example a data processing method. The data processing method is for example performed using technical means, for example a computer. The data processing method is for example executed by or on the computer. The computer for example comprises a processor and a memory in order to process the data, for example electronically and/or optically. The calculating steps described are for example performed by a computer. Determining steps or calculating steps and acquiring steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. A computer for example comprises interfaces in order to receive or output data and/or perform an analogue-to-digital conversion. The data are for example data which represent physical properties and/or are generated from technical signals. The computer is for example operatively coupled to the apparatus in accordance with the ninth aspect, specifically so as to be able to receive, from the detection system, digital signals (the first, second, third and fourth image data) representing the reflections of the light of the first, second, third and type of light, and to conduct the further data processing in accordance with the method according to the first to sixth aspects which is based at least the received image data. The digital signals are generated for example by analogue-to-digital conversion (by known means) of electric signals generated in the detection system upon detection of the reflections.

The expression "acquiring data" encompasses for example (within the framework of a data processing method) the scenario in which the data are determined by the data processing method or program. Determining data for example encompasses measuring physical quantities and transforming the measured values into for example digital data and/or computing the data by means of a computer, for example computing the data within the method of the invention. The meaning of "acquiring data" for example also encompasses the scenario in which the data are received or retrieved by the data processing method or program, for example from another program, a previous method step or a data storage medium, for example for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are for example detected or captured (for example, by an analytical device). The data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired.

BRIEF DESCRIPTION OF THE FIGURES

In the following, aspects and their embodiments according to the present invention are described with reference to the figures, without limiting the present invention to the features which are described in the following and shown in the figures, wherein.

DESCRIPTION OF EXEMPLARY EMBODIMENTS

Figure 1:
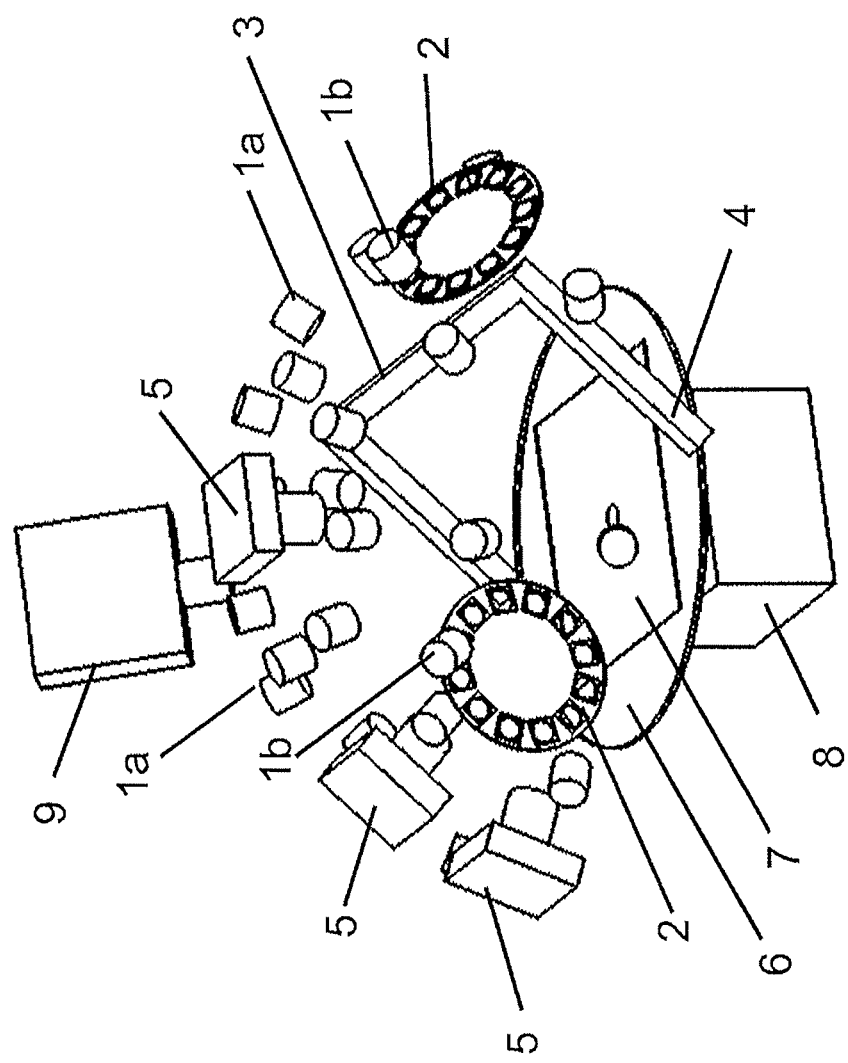
FIG. 1 illustrates a first view of the apparatus in accordance with the second embodiment of the ninth aspect.

As shown in FIG. 1, the apparatus in accordance with the second embodiment of the ninth aspect comprises a plurality of first light sources embodied by white LEDs 1a, a plurality of second light sources embodied by white LEDs 1b fitted with a variable colour filter 2 (i.e. a colour filter 2 which is adjustable regarding the transmitted colour), and a third light source embodied by a linear light source 3. A projector 9 is provided as the fourth light source for irradiating the structure 7 with structured light. The linear light source is a linear array (a line) of white LEDs attached at least one arm 4 (in this case, two arms 4). The at least one arm 4 is driven by a conventional motor (for example, a stepping motor) so as to be moved over the position of a flat structure 7 for irradiating the reflecting surface (the upper surface of the structure 7 facing the first, second, third and fourth light sources) in discrete steps representing a quasi-continuous movement. Thereby, the reflecting surface can be continuously irradiated with light of the third type. The detection system comprises three digital cameras 5 which are configured to generate monochrome (greyscale) image information which allows for detection of brightness values by analysing image contrasts. The structure 7 is disposed on a support structure embodied by a turntable 6 which can be rotated by a driving a stepping motor contained in the base part 8.

Figure 2:
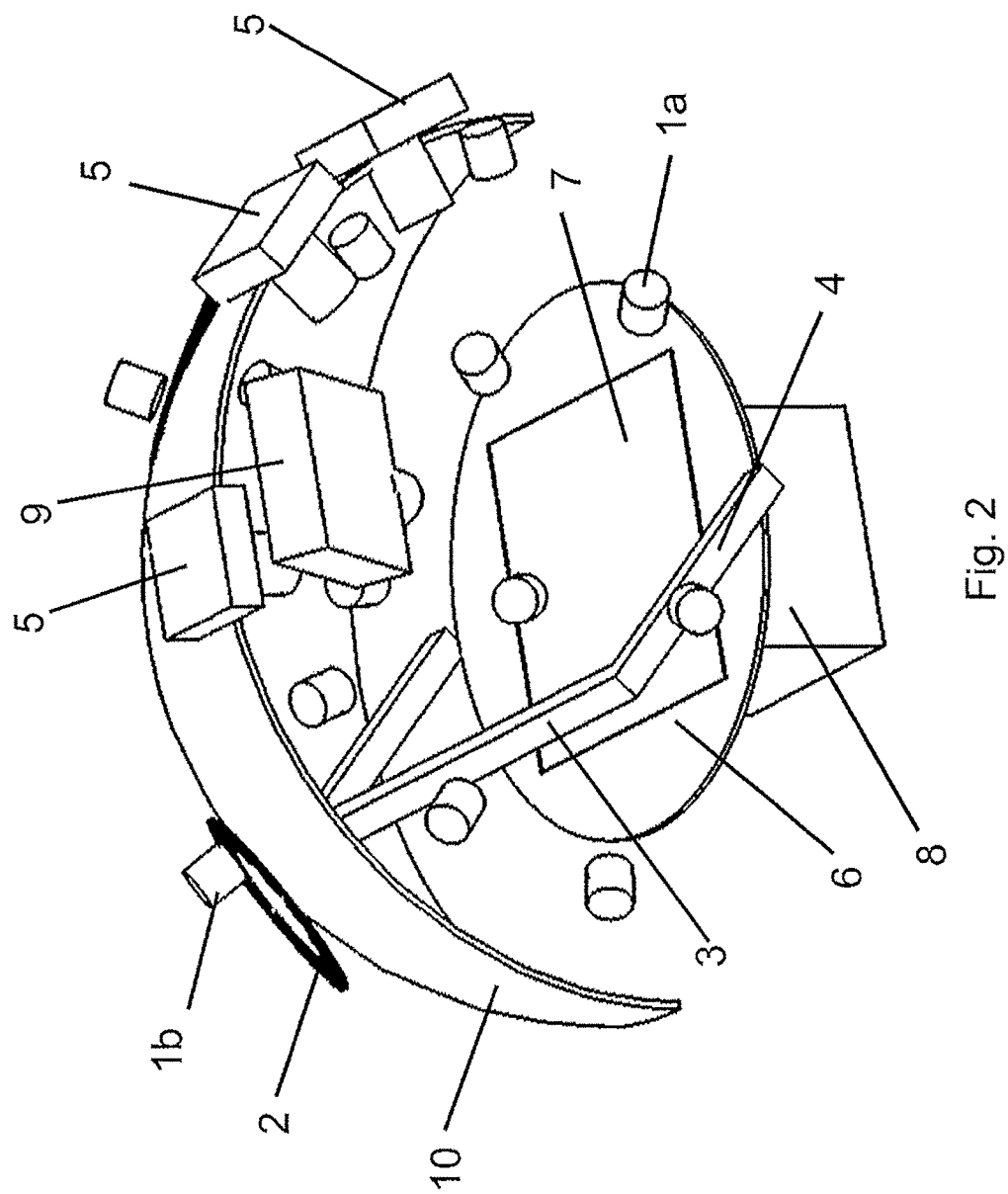
FIG. 2 illustrates a second view of the apparatus in accordance with the second embodiment of the ninth aspect.

As shown in FIG. 2, the LEDs 1a, 1b, colour filters 2, cameras 5 and projector 9 are disposed on a holding part embodied by a cupola-shaped dome (i.e. a shell of a hemisphere) 10. The dome 10 has openings so as to allow the light sources to emit light onto the structure 7 and the cameras 5 to detect reflection signals from the structure 7. The dome 10 is disposed above the structure 7 for reflection measurement on the structure 7.

Figure 3:
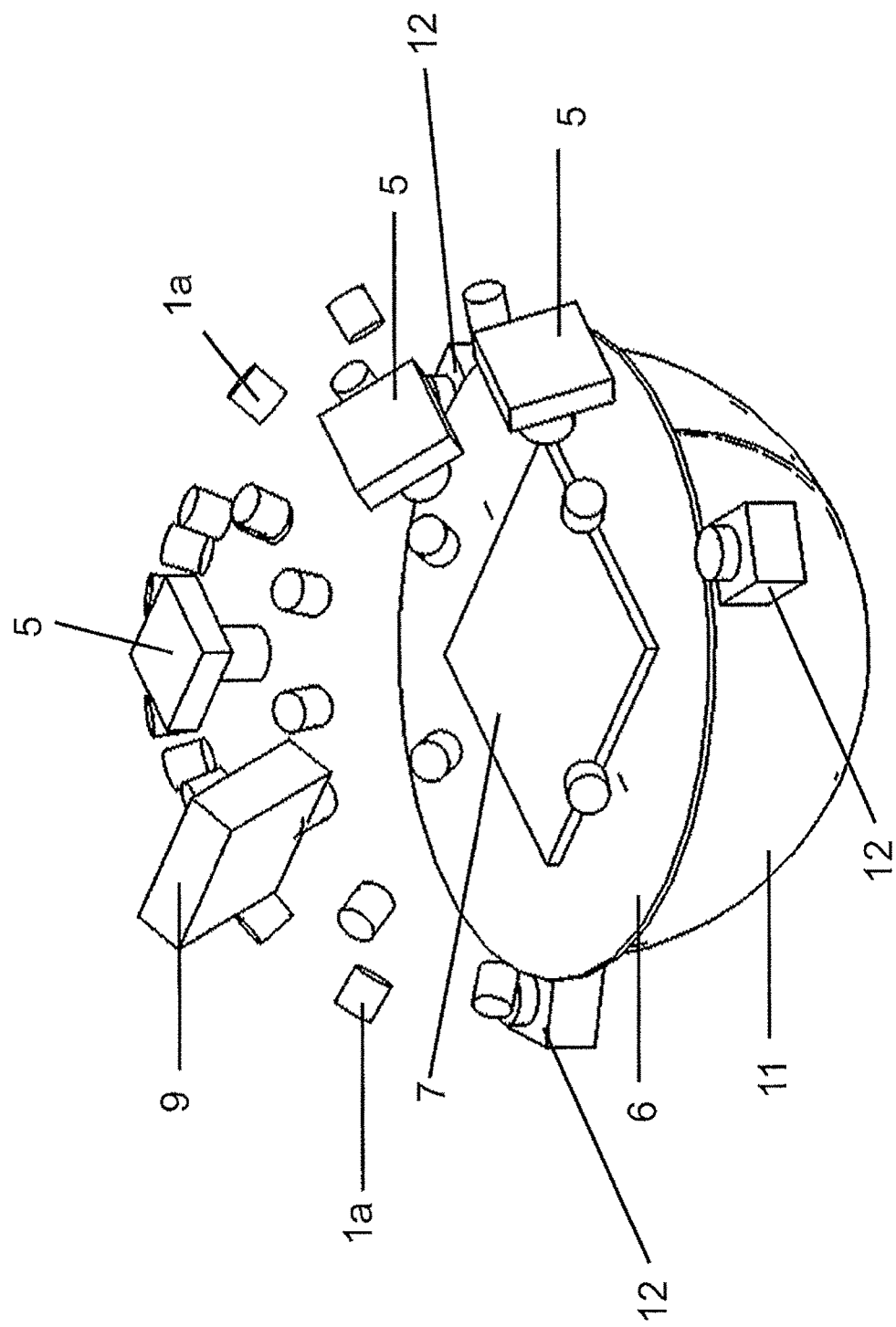
FIG. 3 illustrates a view of the apparatus in accordance with the third embodiment of the ninth aspect.

As shown in FIG. 3, the apparatus in accordance with the third embodiment of the ninth aspect comprises not only the feature describes in the context of FIGS. 1 and 2. In addition thereto, it comprises a second holding embodied by dome 11 below the structure 7. The turntable 6 is driven by at least one motor (for example, a stepping motor) 12 (in this case, three stepping motors 12) which is fastened to a support for the turntable 6.

Figure 4:
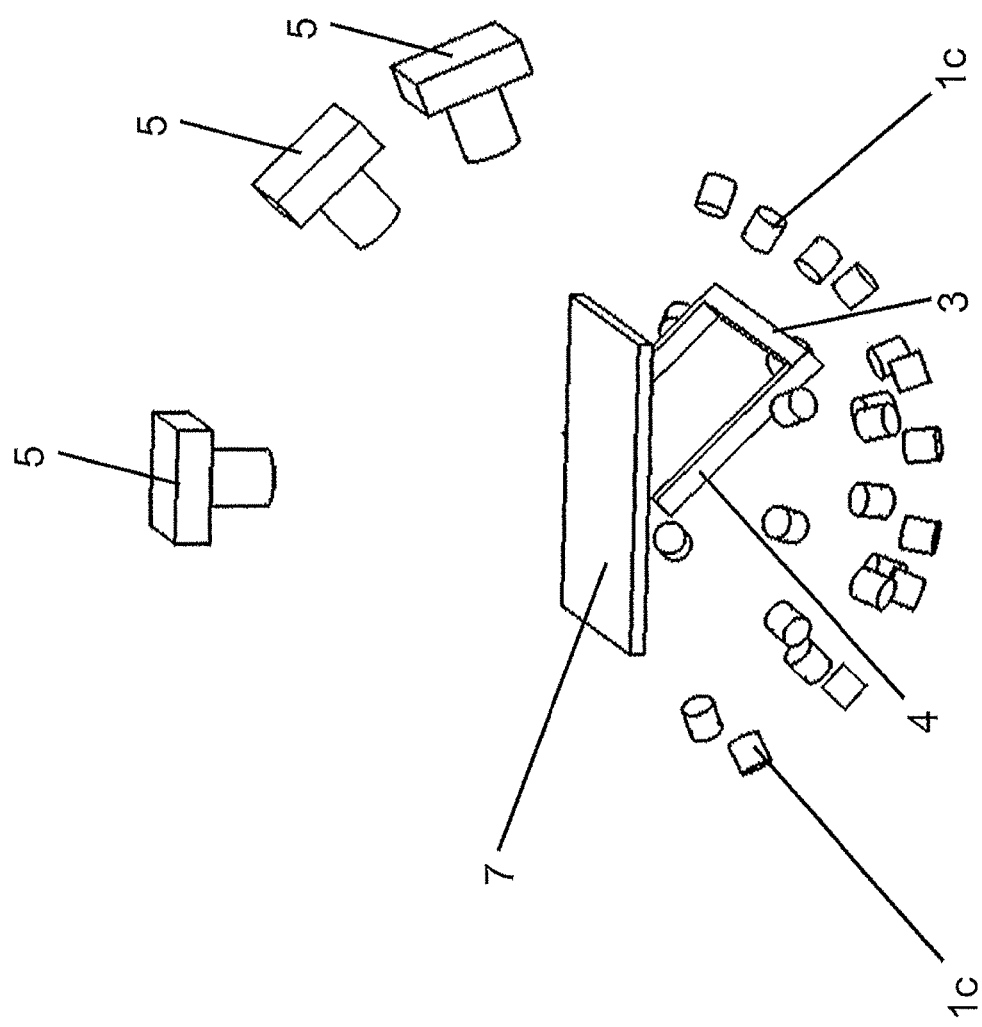
FIG. 4 illustrates a view of the apparatus in accordance with a first example of the third embodiment of the ninth aspect.

In a first example of the third embodiment of the ninth aspect shown in FIG. 4, the second dome 11 is provided with point light sources 1c which may be white LEDs or coloured (spectral) LEDs or a mixture of both which are configured to irradiate the structure 7 with point light from below. In addition, the third light source 3 is disposed so as to be movable below the structure 7. The second dome 11 may also be fitted with the other features (such as the white LEDs 1b provided with colour filters 2—for example instead of the coloured LEDs 1c, the projector 9 and possibly additional cameras 5) with which the first dome 10 is provided. The cameras 5 are provided in the first dome 10 at positions on the other side of the structure 7 when viewed from the position of the LEDs 1c. The third light source 3 may be provided twice, once in the upper hemisphere above the structure 7, and once in the lower hemisphere below the structure 7. However, it is also within the framework of the invention that the third light source is provided only once and is disposed such that it is free to be moved (rotated) through both the lower and the upper hemisphere. In that case, the support part (turntable 6) would have to be disposed accordingly, being held for example by at least one driving part lying on the rotational axis of the third light source 3 and guided at least partly through the at least one arm 4 so as to be able to be coupled to and drive the turntable 6. The cameras 5 being disposed on the other side of the structure 7 when viewed from the position of the LEDs 1c again allow for transparency and/or translucence measurements of the structure 7.

Figure 5:
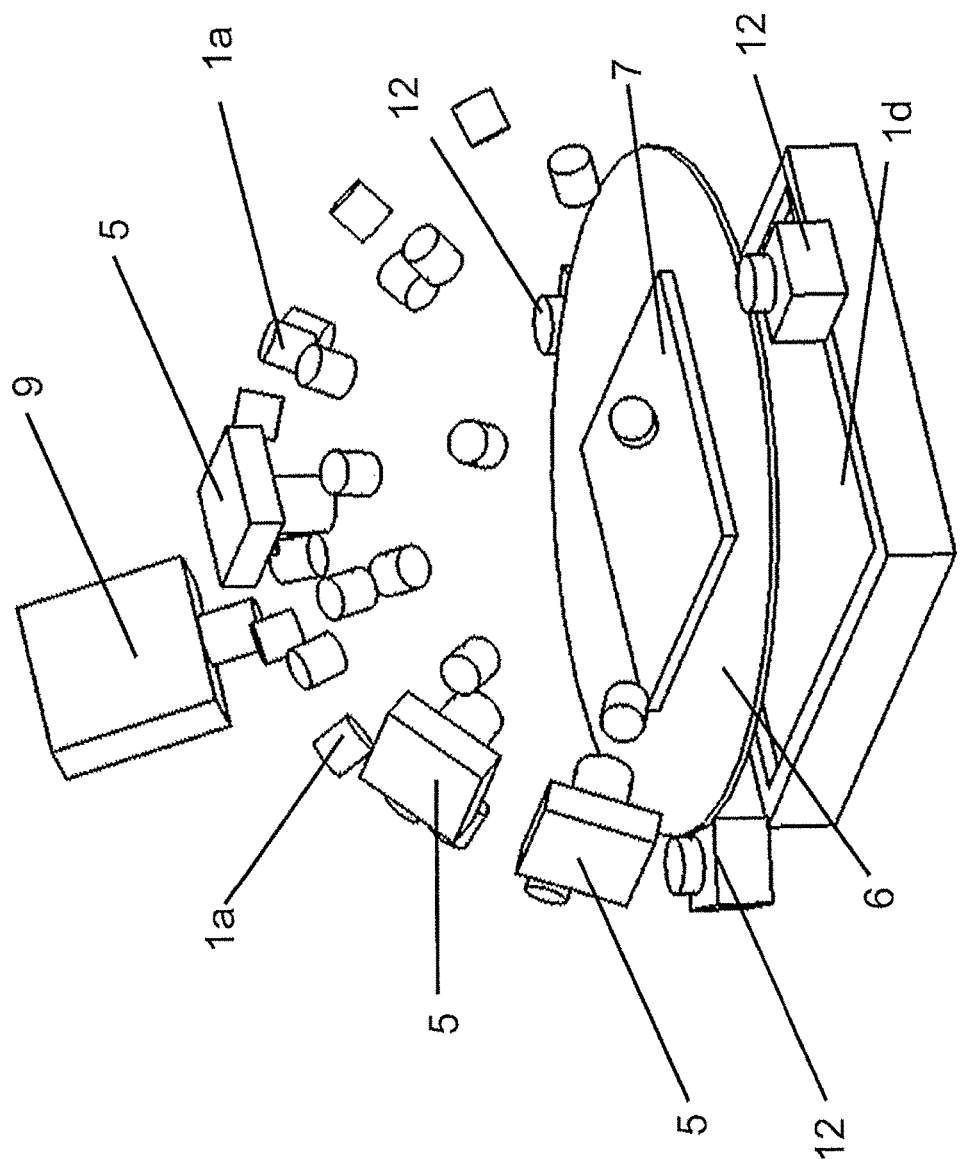
FIG. 5 illustrates a view of the apparatus in accordance with a second example of the third embodiment of the ninth aspect.

FIG. 5 shows a second example of the third embodiment of the ninth aspect. Instead of the second dome structure 11, a planar third light source 1d is provided in the lower hemisphere on the other side of the structure 7 when viewed from the positions of the cameras 5, thereby also allowing for translucence and transparency measurements of the structure 7. The planar light source 1d is embodied by a standard LCD monitor which—if appropriately controlled—is able to provide the functionality of both the first light source and the second light source and a third light source in the lower hemisphere. This avoids having to provide the linear light source 3 as an LED array or a fluorescent tube and the associated driving and holding mechanism. The linear light source 3 may be provided by the monitor by displaying a line-shaped bright image at predetermined pixel positions. The pixel positions may be changed while irradiating the structure 7 from below, thereby simulating movement of the linear light source 3 below and along the position of the structure 7. Compared to the arrangement of FIGS. 1 to 4, using a display device such as a monitor instead of the other alternatives for the linear light source 3 provides greater flexibility and allows for simplified construction of the apparatus. Instead of a monitor, a large two-dimensional (planar) array of controllable coloured LEDs (which are able to emit both white and spectral light) may be used as the planar third light source 1d.

Figure 6:
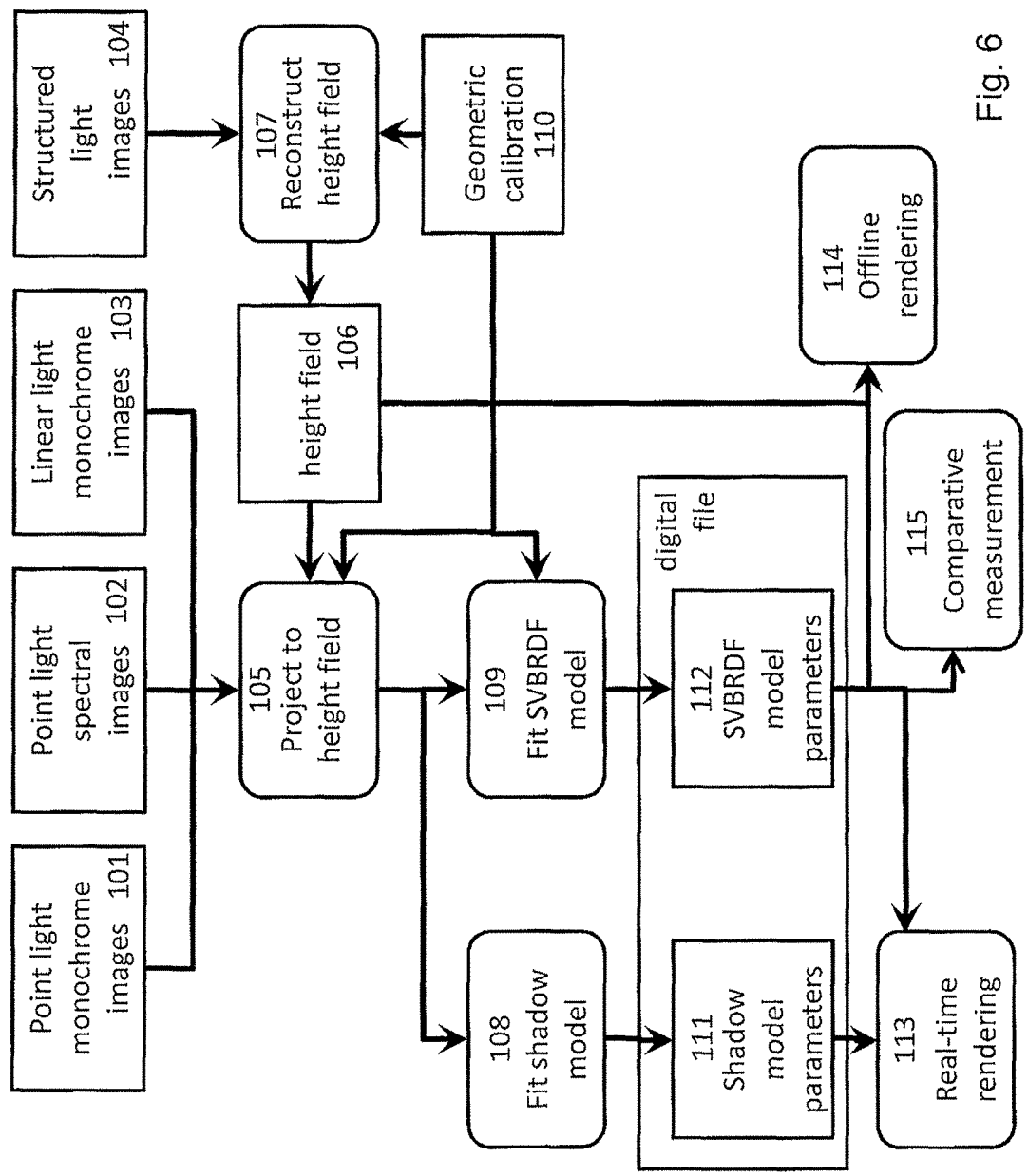
FIG. 6 illustrates a flow diagram of the method in accordance with the first embodiment of the first aspect.

The flow diagram of FIG. 6 shows the method in accordance with the first embodiment of the first aspect. Step 101 encompasses acquisition of the first image data describing at least one point light monochrome image, step 102 encompasses acquisition of the second image data describing at least one point light spectral image, step 103 encompasses acquisition of the third image data describing at least one linear light monochrome image, and step 104 encompasses acquisition of the fourth image data describing at least one structured light image.

After applying high dynamic range (HDR) combination and radiometric correction of the raw images, a set of calibrated images of the reflecting surface of the structure 7 made of a certain material is received. These can be grouped by the different illumination conditions in the apparatus according to the ninth aspect. On the one hand there are monochrome images of the material captured using either the point light sources 1a, 1b, 1c, 1d, the linear light source 3, 1d in its different positions or lit by the patterns emitted by the projector 9. On the other hand there are a few colour or spectral images generated using colour filters (the filter wheel systems) 2. In one further example and additionally, geometric calibration data of the apparatus is available, containing detailed information about the placement of all components for each of the images. The geometric calibration data is acquired in step 110.

In step 107, a height field for the material is reconstructed from the structured light images acquired in step 104. First, a point cloud is generated using a standard method from the prior art, an overview being given by Salvi, J. et al., A state of the art in structured light patterns for surface profilometry, Pattern Recognition 43, no. 8 (2010): pp. 2666-2680 utilizing the pattern images and the geometric calibration of the cameras. Afterwards, a height value for each pixel on the material reference plane is generated, forming the height field which is acquired as the surface geometry data in step 106. For this, all points p from the point cloud are perpendicularly projected to a reference plane and their distance to the plane (their height) is measured. This leads to a set of projected coordinates p' and corresponding heights h. For each pixel (x,y) on the reference plane a set of k nearby points $P=\{p_i'\}$ is gathered and a height value for (x,y) is generated using filtering on the corresponding heights $h_i$:

$$h_{x,y} = \frac{1}{\sum_{p_i' \in P} F(\|p_i' - (x, y)\|_2)} \sum_{p_i' \in P} F(\|p_i' - (x, y)\|_2) h_i, \quad (1)$$

where F is a filter kernel. e.g. the Gaussian normal distribution function and $\|\cdot\|_2$ is the Euclidean distance.

After the height field reconstruction all other images are projected in step 105 to the height field to align all images in a common coordinate system, meaning that the same pixel in all projected images corresponds to the same location on the materials surface. Thereby, the reflecting surface mapping data (specifically, the mapping described in the context of the method in accordance with the first aspect) is determined.

The projected images are then fed to the SVBRDF fitting which is encompassed in step 109 which will seek a set of parameters for a given BRDF model for each pixel (x,y) on the material reference plane. This map of parameters is determined in step 112 and is then stored e.g. in a digital (electronic) file and can be fed to the image generation process, either real-time rendering encompassed in step 113, offline rendering encompassed in step 114 or further processing within in the method in accordance with the sixth aspect by conducting the comparative measurement for quality control of an optical property of the material in step 115. The processing in step 109 allows to eliminate the influence of a fixed illumination geometry of the apparatus and the specific geometry of the structure 7 (specifically, of the reflecting surface) when determining the reflectance distribution data.

For the real-time rendering, the describing self-shadowing inside of the material can also be extracted from the projected images by finding in step 108 per-pixel parameters for a shadow model which are stored in a second map in step 111 in the digital file.

SVBRDF Fitting

The SVBRDF fitting process of step 109 can be roughly divided into two phases. In the first phase, the data is prepared and in the second phase the per-pixel BRDF model parameters are found by a fitting process. The BRDF fitting process is different from previously published ones since it separates fitting of the BRDF 4D "shape" from the fitting of the colour components of the model to cope with the sparse colour information.

The first phase starts by computing monochrome information from the available colour samples. This requires knowledge of the spectral response of the capture system (detection system). In the case of spectral samples this involves computing a convolution of all image spectra with the spectral system response of the monochrome imaging part. In the case of trichromatic colour images, a 1×3 matrix is computed based on the spectral response corresponding to the trichromatic colour space, on the spectral system response of the monochrome imaging part and on some training data. A monochrome image is then computed by left-multiplying the matrix to all colour vectors (pixels) of the colour image.

In a second step, a set of pixels is selected for joint fitting of the BRDF parameters. In the simplest case this can consist of only a single pixel each time. However, pixels might also be grouped by their appearance using a clustering technique. This helps to stabilize fitting since then more data is available to the fitting phase.

In a further (the last) step of the preparation phase consists of an extraction of data values corresponding to the selected pixels. For this, the pixel values of the respective pixels are extracted from the images and the geometric calibration data and the height field are used to compute the position of light sources and sensors with respect to the single pixels.

This data is then fed into the second phase that does the real BRDF fitting (fitting of bidirectional reflectance distribution function parameters). This comprises fitting of a monochrome BRDF followed by "colourizing" this monochrome BRDF afterwards. The result of this process is the set of parameters per pixel, consisting of the surface normal vector, the specular parameters of the model and the colour values for the BRDF model.

Monochrome BRDF Fitting

The fitting of the monochrome BRDF model can be seen as an energy minimization problem where one seeks to find a set of parameters for the BRDF model in such a way that a simulation of the measured material using this BRDF model matches the measured values with minimal error using a certain distance measure. However, when trying to solve this problem in a straightforward manner one encounters a difficult problem: the resulting energy function may have a lot of local minima where all practically applicable algorithms easily get stuck. For this reason, a good initialization for the BRDF model parameters is required, to start the optimization as near as possible to the optimal result. Furthermore, it is mandatory to restrict the optimizer to certain descent directions in the parameter space at one time.

The solution included in the disclosed method starts with a closed form initialization for the surface normal and the diffuse albedo (the diffuse "colour" for the monochrome BRDF). For rather dull materials this is done using the well-known photometric stereo technique described in Woodham, Robert J., Photometric stereo: A reflectance map technique for determining surface orientation from image intensity, 22nd Proc. SPIE 0155, Image Understanding Systems and Industrial Applications 1, 136 (Jan. 9, 1979), pp. 136-143. For more specular materials the maximum measurement value generated by the linear light source illumination is searched for all rotations of the sample. Assuming a perfectly specular material the normal vector can then be computed from the law of reflection. The user can select the appropriate algorithm. By setting the specular colour to zero and the specular parameters to some average values (depending on the model used), a complete initialization of the per-pixel parameters is obtained.

After this initialization, the parameters and the data are fed into the main optimization loop consisting of an optimization of diffuse and specular parameters only followed by an optimization of the normal vector only. Afterwards, a check for convergence is made. If the decrease in error obtained during the last steps is below a given (for example predetermined or user-specified) threshold, the algorithm is terminated. Otherwise the loop is started again.

Fitting Steps

Despite constraining the optimization to different subsets of parameters of the per-pixel parameters, the optimization of specular and diffuse parameters as well as the optimization of the normal vector is performed in the same manner. An optimization loop is employed in which the first step is to synthesize measurement values from the given set of per-pixel parameters. This is essentially the simulation of the measurement device on the virtual material. Technically, this is done by solving the rendering equation for each pixel and each illumination condition in question. The rendering equation is described for example in Kajiya, James T., The rendering equation, ACM SIGGRAPH Computer Graphics, vol. 20, no. 4. ACM, pp. 143-150, 1986. For this a virtual scene is constructed from the calibration and the exitant radiance in direction of the sensor is computed as follows:

$$L_o(x,\omega_o) = L_e(x,\omega_o) + \int_{\omega_i \in \Omega} \rho(p_x, \omega_o, \omega_i) L_i(x, \omega_i)(n_x \cdot \omega_i) d\omega_i \qquad (2),$$

where x is a position on the surface, $\omega_o$ is the outgoing direction, $L_e$ is the radiance emitted by a surface, $\Omega$ is the local hemisphere over the point x, $\omega_i$ is the direction of incoming light, $n_x$ is the local surface normal at x, $\rho$ is the selected BRDF model and $p_x$ is the set of pixel parameters. Equation (2) is recursive since the incident radiance $L_i(x, \omega_i)$ equals the exitant radiance $L_o(x', -\omega_i)$ at the point x' in the scene visible in direction $\omega_i$.

To simplify the synthesis process, the method considers only the first level of the recursion, assuming direct lighting only. The virtual material is assumed to be the only reflecting surface in the scene and the light source is the only emitting surface. When the light sources are additionally discretized to a set of n point light sources, the rendering equation reduces to:

$$L_o(x,\omega_o)=\Sigma_{j=1}{}^n \rho(p_x,\omega_o,\omega_{ij})L_{ij}(x,\omega_{ij})(n_x\cdot\omega_{ij}) \quad (3),$$

where $L_{ij}$ is the emitted radiance of the j-th point light and $\omega_{ij}$ is the direction towards it. After the radiance values have been calculated, they are compared to the measured radiance values and an error value is computed. The error function can e.g. be a relative error or an L1-error.

Afterwards the optimization is checked for convergence. If the decrease of the error value between the last and the current iteration is below a threshold or if a given total number of iterations is reached then the algorithm is terminated. Otherwise, a new set of parameters is computed from the old set in order to reduce the error function. This is done using standard methods like gradient descent and might require additional evaluations of the forward synthesis and error evaluation to numerically compute the gradient of the error function. After parameter refinement the next iteration is started.

Colour Fitting

The final part of the whole algorithm in accordance with the disclosed method is the determination of colours for the monochrome BRDF. The first step is to compute a specular colour from the monochrome specular part. For dielectric materials this is done by copying the monochrome value into all colour channels since those materials have a white highlight. For metals or other conductors different strategies might be employed e.g. incorporating prior knowledge about the material class.

Afterwards, the specular part is removed from all measured values to end up with colour values that contain only diffuse colour information. For this, a forward synthesis like in the previous step is computed only incorporating the specular part of the BRDF model. The resulting synthesized specular colour is then subtracted from the measured colour values.

In a further (the final) step these colour values are input to the diffuse colour fitting. This is cast as a linear least squares problem per colour channel. In the simplest case the error function can be formulated as:

$$E_i(d_i)=\Sigma_{j=1}{}^N w_j \|d_i - m_{i,j}\|_2^2 \quad (4),$$

where N is the number of colour samples, $d_i$ is the diffuse colour value for channel i, $m_{i,j}$ is the measured, specular-free diffuse value for colour channel i and $w_j$ is a weight for sample j. This weight can be computed based on multiple considerations, e.g. the angular distance of the sample to the specular highlight or the saturation of the measured colour. When fitting colours in XYZ colour space (and not spectral) a linear approximation of the well-known $\Delta E^*$ can be utilized to fit a perceptually closer colour. Moreover the RANSAC algorithm might be applied to get rid of outliers.

Shadow Fitting

In off-line rendering methods like ray tracing in step 114, correct self-shadowing inside of the material can be generated in step 108 using the reconstructed height field. However, in real-time rendering applications encompassed by step 113, this approach is not straightforwardly applicable. Of course, techniques like shadow mapping can be employed, but the resulting shadows are rather hard and unnatural.

To generate real-time self-shadowing, the disclosed method fits a second function for each position on the material surface that describes the attenuation in relation to the incoming light direction. The self-shadowing is derived from the comparison of the values of a respective pixel of the projected point-light input images to the synthesized values generated by the forward synthesis using the final BRDF parameters for the same pixel. A mean ratio or a mean difference of the two values per light direction can be used to express the self-shadowing effect.

To model the light-direction-dependent shadow values smooth hemispherical functions like spherical harmonics described in Sloan, Peter-Pike et al., Precomputed radiance transfer for real-time rendering in dynamic, low-frequency lighting environments, ACM Transactions on Graphics (TOG), vol. 21, no. 3, pp. 527-536, ACM, 2002 or polynomial texture maps described in Malzbender, Tom et al., Polynomial texture maps, Proceedings of the 28th annual conference on Computer Graphics and Interactive Techniques, pp. 519-528, ACM, 2001 can be used. However, since a very regular sampling of the hemisphere with point light sources is obtained by the disclosed method and since the inventors noticed that the aforementioned methods show artefacts when extrapolating to grazing angles, the disclosed method employs a different strategy: a small two-dimensional table per pixel is stored in step 111 comprising, e.g. 4×4 entries that are parameterized over a two-dimensional projection of the light hemisphere. The entries of this table are computed by filtering the samples in angular space. At reconstruction time, a two-dimensional linear interpolation is performed. This method has a constant extrapolation towards grazing illumination angles (large angles of incidence) and comparable interpolation in between the sample points compared to the mentioned prior art methods while consuming only slightly more memory per pixel. For level-of-detail rendering, spatially down-sampled versions of the tables can be pre-computed.

Figure 7:
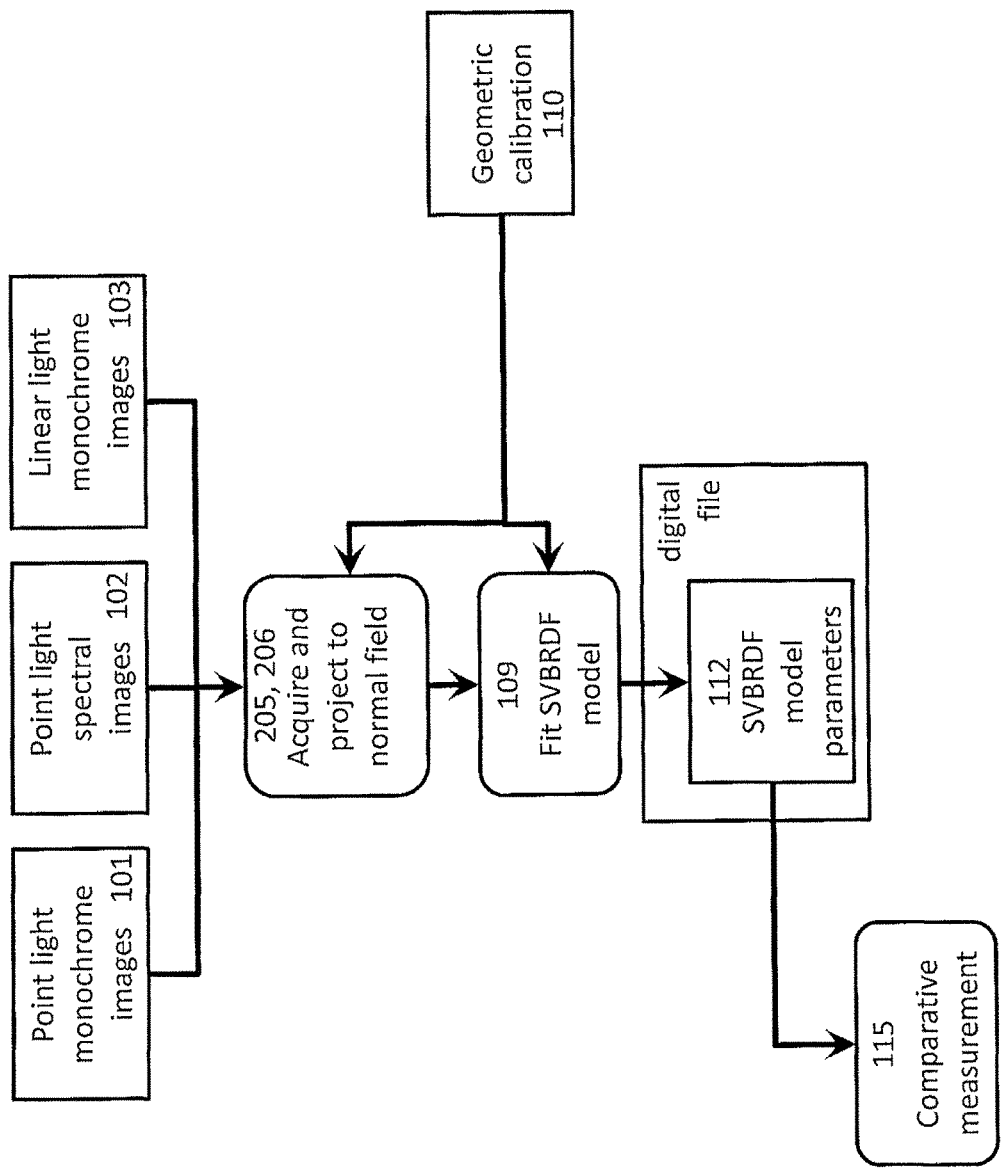
FIG. 7 illustrates a flow diagram of the method in accordance with the second embodiment of the first aspect.

FIG. 7 shows the second embodiment of the method in accordance with the first aspect which is used according to the sixth aspect. Instead of using the height field, a normal field is acquired as the surface geometry data in step 206 and the reflecting surface mapping data is determined in step 205 by projecting the images described by the first image data, second image data and the third image data to the normal field. The remaining steps shown FIG. 7 having the same designations as those shown in FIG. 6 encompass the same data processing functionalities as the corresponding steps shown in and described above with reference to FIG. 6.

The invention claimed is:

1. A system for obtaining data representing optical signals received from a reflecting surface of a structure, comprising:
 a) at least one first light source comprising a broadband point light source oriented toward the reflecting surface;
 b) at least one second light source comprising a spectrally variable point light source oriented toward the reflecting surface;
 c) at least one third light source comprising a linear broadband light source mounted on a movable arm and oriented toward the reflecting surface;
 d) a dome enclosing the movable arm and at least one third light source;
 e) a support part for supporting the structure enclosed within the dome;
 f) a detection system configured to
    detect a first reflection signal of the first light source from the reflecting surface and to convert the first reflection signal into first image data describing an image of the reflecting surface of the structure;
    detect at least one second reflection signal of the second light source from the reflecting surface and to convert the second reflection signal into second image data describing an image of the reflecting surface of the structure; and detect at least one third reflection signal of the third light source from the reflecting surface and to convert the third reflection signal into third image data describing an image of the reflecting surface of the structure; and g) a computer which is operatively coupled to the detection system and configured to execute a computer program which, when running on the computer or when loaded onto the computer, causes the computer to perform the following data processing steps:

h) acquiring the first image data;

i) acquiring the second image data;

j) acquiring the third image data;

k) acquiring surface geometry data describing a three-dimensional surface geometry of the reflecting surface; and l) determining, based on the first image data and the second image data and the third image data and the surface geometry data, reflecting surface mapping data describing a mapping between the reflections described by the first image data, the second image data and the third image data, and the three-dimensional surface geometry of the reflecting surface.

2. The system according to claim 1, comprising at least one fourth light source comprising a structured light source oriented toward the reflecting surface;

wherein the detection system is configured to detect a fourth reflection signal of the fourth light source from the structure and to convert the fourth reflection signal into surface geometry data describing a height field of the structure.

3. The system according to claim 1, wherein the detection system and the first light source, the second light source, and the third light source are disposed in the dome above the support part and at least one further light source is disposed in a hemisphere below the support part.

4. The system according to claim 2, wherein the detection system and the first light source, the second light source, the third light source and the fourth light source are disposed in the dome above the support part and at least one further light source is disposed in a hemisphere below the support part.

5. A computer-implemented digital data processing method of determining data representing a mapping of optical signals described by image data of a reflecting surface of a structure to a three-dimensional surface geometry of the reflecting surface, the method comprising the following steps which are executed by a computer:

a) acquiring first image data describing an image of a reflection of a point source of broadband light from the reflecting surface;

b) acquiring second image data describing an image of a reflection of a point source of spectrally variable light from the reflecting surface;

c) moving an arm and acquiring third image data describing an image of a reflection of a linear source of light mounted on the arm from the reflecting surface;

d) acquiring surface geometry data describing a three-dimensional surface geometry of the reflecting surface; and e) determining, based on the first image data and the second image and the third image data and the surface geometry data, reflecting surface mapping data describing a mapping between the reflections described by the first image data, the second image data and the third image data, and the three-dimensional surface geometry of the reflecting surface.

6. The method according to claim 5, wherein the surface geometry data describes a height field of the reflecting surface.

7. The method according to claim 6, further comprising: acquiring fourth image data describing an image of a reflection of structured light, wherein the surface geometry data is acquired based on the fourth image data.

8. The method according to claim 5, wherein the surface geometry data describes at least one of a normal field and a height field of the reflecting surface.

9. The method according to claim 8, wherein the surface geometry data describes a normal field of the reflecting surface and is acquired based on at least one of the first image data, second image data and third image data.

10. A computer-implemented method of determining data describing a spatially varying bidirectional reflectance distribution of a reflecting surface of a structure, the method comprising the following steps which are executed by a computer:

performing the method according to claim 5;

acquiring reflectance function data describing a bidirectional reflectance distribution function model; and determining, based on the reflecting surface mapping data and the reflectance function data, reflectance distribution data describing a spatially varying bidirectional reflectance distribution of the reflecting surface.

11. A computer-implemented method of offline rendering of a digital image representation of a reflecting surface of a structure, the method comprising the following steps which are executed by a computer:

performing the method according to claim 10;

determining, based on the reflectance distribution data and at least one of the first image data, second image data and third image data, surface representation data describing an image of the reflecting surface; and offline rendering, on a display device, of the information content of the surface representation data.

12. A computer-implemented method of determining data describing a shadow appearance of a reflecting surface of a structure, the method comprising the following steps which are executed by a computer:

performing the method according to claim 10; and determining, based on the reflecting surface mapping data and at least one of the first image data, second image data and third image data, shadow appearance data describing a model and parameters defining a shadow appearance of the reflecting surface.

13. A computer-implemented method of real-time rendering of a digital image representation of a reflecting surface of a structure, the method comprising the following steps which are executed by a computer:

performing the method according to claim 10; and determining, based on the reflectance distribution data, surface representation data describing an image of the reflecting surface; and real-time rendering, on a display device, of the information content of the surface representation data.

14. A non-transitory computer-readable storage medium including a computer program which, when running on a computer or when loaded onto a computer, causes the computer to perform the following data processing steps:

a) acquiring first image data describing an image of a reflection of a point source of broadband light from the reflecting surface;

b) acquiring second image data describing an image of a reflection of a point source of spectrally variable light from the reflecting surface;

c) moving an arm and acquiring third image data describing an image of a reflection of a linear source of light mounted on the arm from the reflecting surface;

d) acquiring surface geometry data describing a three-dimensional surface geometry of the reflecting surface; and e) determining, based on the first image data and the second image and the third image data and the surface geometry data, reflecting surface mapping data describing a mapping between the reflections described by the first image data, second image data and third image data, and the three-dimensional surface geometry of the reflecting surface.

15. The system according to claim 3, wherein the detection system is further configured to convert light transmitted through the structure into transmissive image data of the structure.

16. The system according to claim 4, wherein the detection system is further configured to convert light transmitted through the structure into transmissive image data of the structure.

* * * * *